(12) United States Patent
Chinnadurai et al.

(10) Patent No.: US 9,907,817 B1
(45) Date of Patent: Mar. 6, 2018

(54) BIOMIMETIC SYNTHESIS OF ANTIHYPERGLYCEMIC SILVER NANOPARTICLES

(71) Applicant: KING SAUD UNIVERSITY, Riyadh (SA)

(72) Inventors: Veeramani Chinnadurai, Riyadh (SA); Khalid S. Al-Numair, Riyadh (SA); Mohammed A. Alsaif, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 15/705,196

(22) Filed: Sep. 14, 2017

(51) Int. Cl.
| | |
|---|---|
| *A61K 9/14* | (2006.01) |
| *A61K 9/16* | (2006.01) |
| *A61K 33/38* | (2006.01) |
| *A61K 36/185* | (2006.01) |
| *B82Y 40/00* | (2011.01) |
| *C01G 5/00* | (2006.01) |
| *A01H 5/02* | (2018.01) |
| *A61K 36/18* | (2006.01) |

(52) U.S. Cl.
CPC ........... *A61K 33/38* (2013.01); *A01H 5/0216* (2013.01); *A61K 9/141* (2013.01); *A61K 9/16* (2013.01); *A61K 9/1664* (2013.01); *A61K 36/18* (2013.01); *A61K 36/185* (2013.01); *B82Y 40/00* (2013.01); *C01G 5/00* (2013.01)

(58) Field of Classification Search
CPC ...... A61K 33/38; A61K 36/185; A61K 9/141; A61K 9/16; A61K 9/1664; B82Y 40/00; C01G 5/00
See application file for complete search history.

(56) References Cited

U.S. PATENT DOCUMENTS

| | | | |
|---|---|---|---|
| 8,057,682 B2 * | 11/2011 | Hoag | B22F 1/0018 210/688 |
| 9,428,399 B1 | 8/2016 | Awad et al. | |
| 9,637,807 B1 * | 5/2017 | Awad | A61K 33/38 |
| 2017/0100338 A1 | 4/2017 | Awad et al. | |

FOREIGN PATENT DOCUMENTS

JP 4229942 2/2009

OTHER PUBLICATIONS

Amit Kumar Mittal, Yusuf Chisti, and Uttam Chand Banerjee, "Synthesis of metallic nanoparticles using plant extracts", Biotechnology Advances, 2013, 31(2), 346-356. (Year: 2013).*
Ali Alkandi et al., "Antidiabetic Activity of Zinc Oxide and Silver Nanoparticles", International Journal of Molecular Sciences (15) pp. 2015-2023 (2014).
Mani Rupeshkumar et al., "Role of Herbal Plants in the Diabetes Mellitus Therapy: An Overview", International Journal of Applied Pharmaceutics (6)3 pp. 1-3 (2014).
S. Balasubramanian et al., "Green Synthesis of Silver Nanoparticles Using Cressa Cretica Leaf Extract and its Antibacterial Efficacy", IJACSA pp. 1-7 (2015).
Shanker Kalakotia et al., "Herbal Drugs and Herbal Mediated Silver Nano Particles as Anti Diabetics: A New Horizon", Int. J. Pharm. Sci. Rev. Res., 31(2) pp. 142-148 (2015).

* cited by examiner

*Primary Examiner* — John Pak
*Assistant Examiner* — Nathan W Schlientz
(74) *Attorney, Agent, or Firm* — Richard C. Litman

(57) ABSTRACT

A biomimetic synthesis of antihyperglycemic nanoparticles using silver nitrate and *Lavatera cretica* is a method for the green synthesis of silver nanoparticles. These nanoparticles may be produced by extraction of fresh *L. cretica* leaves and mixing and incubation of the resulting *L. cretica* extract with silver nitrate to produce a nanoparticle composition including the silver nanoparticles. The nanoparticle composition may protect against hyperglycemia.

12 Claims, 6 Drawing Sheets

BIOMIMETIC SYNTHESIS OF ANTIHYPERGLYCEMIC SILVER NANOPARTICLES

BACKGROUND

1. Field

The disclosure of the present patent application relates to nanotechnology, and particularly to a biomimetic synthesis of nanoparticles using silver nitrate and *Lavatera cretica*.

2. Description of the Related Art

Recently, metal nanoparticles have demonstrated important uses in a variety of fields. In particular, silver nitrate derived nanoparticles have been of interest to researchers, due to their wide range of applications including electronics, biosensing, plasmonics, optics, and medicine.

Synthesis of silver nanoparticles (AgNPs) have been achieved by a variety of methods, including physicochemical, thermal decomposition, electrochemical, microwave assisted, sonochemical, solvothermal, photosynthesis, photochemical reduction, chemical reduction and continuous-flow methods. These methods are often costly or produce byproducts that pose increased risks to human health and the environment.

Thus, an affordable method of biologically synthesizing silver nanoparticles solving the aforementioned problems is desired.

SUMMARY

The biomimetic synthesis of antihyperglycemic AgNPs using silver nitrate and *Lavatera cretica* includes providing a solution including silver nitrate; providing an extract of the *Lavatera cretica* plant or plant part; mixing the silver nitrate solution and the extract solution to form an aqueous mixture; and resting the aqueous mixture for a period of time to form *L. cretica* AgNPs. The AgNPs may be used for their protective effect against hyperglycemia. The synthesis method is inexpensive and environmentally friendly.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
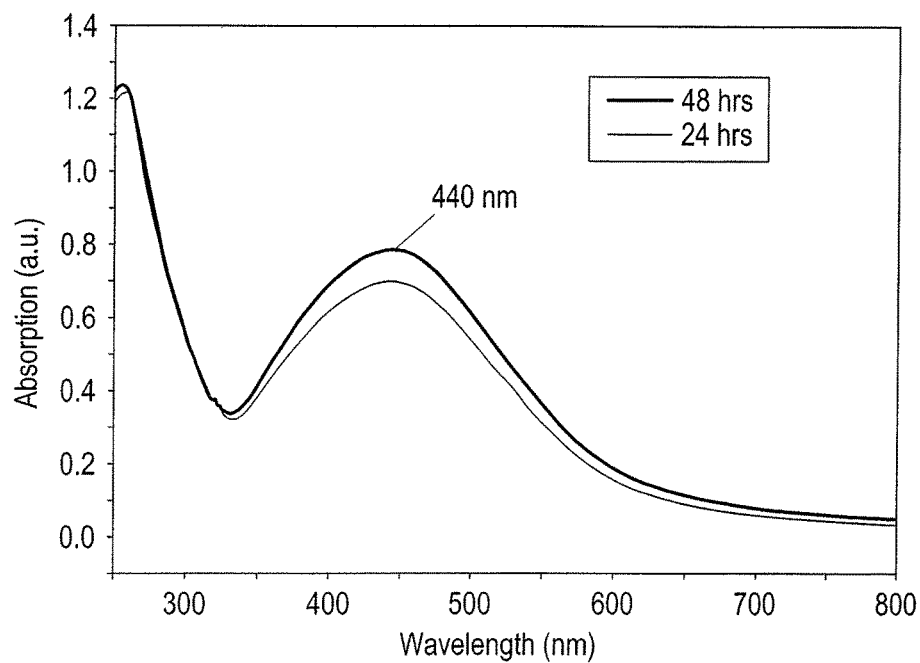
FIG. 1 is the UV-Visible spectrum of *L. cretica* AgNPs after about 24 hours and about 48 hours of incubation.

Biomimetic synthesis of antihyperglycemic nanoparticles can include mixing silver nitrate with an extract of *Lavatera cretica* (*L. cretica*) to provide silver nanoparticles (AgNPs). The extract can be an aqueous leaf extract of *L. cretica*. The nanoparticles can be spherical in shape with sizes ranging from about 5 nm to about 24 nm (average size about 11 nm).

The extract can be prepared by collecting one or more plant parts of the *L. cretica* plant for use as the extraction substrate. Suitable plant parts can include, for example, the leaves, flowers, stems, and/or roots, of *L. cretica*. Prior to extraction, the *L. cretica* plant or plant part may be washed thoroughly one or more times with tap water and/or distilled water, e.g., triple distilled water. The washed *L cretica* may then be dried, e.g., shade dried, at room temperature to provide dried *L cretica*. The shade drying may proceed for about two days. The dried *L. cretica* may then be powdered, by grinding, blending, or any other conventional means. Powdered *L. cretica* may then be suspended in water, e.g., triple distilled water to produce the *L. cretica* extract. For example, about 5 grams of the powdered *L. cretica* may be suspended in about 500 mL of triple distilled water for about 24 hours. The *L. cretica* extract may be filtered using filter paper, a muslin cloth, or any other conventional means, producing filtered *L. cretica* extract.

The biomimetic synthesis of the AgNPs may be achieved by mixing the *L. cretica* extract with silver nitrate ($AgNO_3$). For example, about 10 mL of the filtered *L. cretica* extract can be mixed with about 250 mL of the $AgNO_3$. The mixture may be incubated at room temperature in a darkened location until its color changes from colorless to brown, indicating the formation of AgNPs. The mixture may then be centrifuged, e.g., at about 15,000 rpm for about 20 minutes, and re-suspended in distilled water. The centrifugation and resuspension steps may then be repeated multiple times in order to remove impurities. The final resuspension may then be dried using conventional means such as an oven, producing *L. cretica* AgNPs or a nanoparticle composition including AgNPs and *L. cretica* extract components.

The nanoparticle composition including AgNPs and *L. cretica* extract components can be administered to a patient in need thereof. For example, a therapeutically effective amount of the composition can be administered to a patient suffering from Diabetes mellitus (diabetes) and/or hyperglycemia. The therapeutically effective amount can be about 1 mg/kg.

The nanoparticle composition can be admixed with a suitable pharmaceutical carrier, including, but not limited to water, glycols, oils, alcohols, flavoring agents, preservatives, coloring agents, starches, sugars, diluents, granulating agents, lubricants, binders, disintegrating agents, and the like. The composition can be administered by any conventional route of administration, including, but not limited to, intravenous, oral, subcutaneous, intramuscular, intradermal and parenteral. Depending on the route of administration, the composition can be constituted into any form. For example, forms suitable for oral administration include as pills, gelcaps, tablets, caplets, capsules (each including immediate release, timed release and sustained release formulations), granules, powders, and syrups.

Example 1

Extraction of *L. cretica* Leaves

Leaves were collected from fresh *L. cretica* from Riyadh, Saudi Arabia. An aqueous extraction was performed using the leaves to produce *L cretica* leaf extract. The leaves were washed first with tap water and then with triple distilled water. The washed *L. cretica* leaves were shade dried for about two days. The shade dried *L. cretica* leaves were then powdered using a blender. 5 grams of powered *L. cretica* leaves were suspended in 500 mL of triple distilled water for 24 hours, producing *L. cretica* leaf extract. The *L. cretica* leaf extract was filtered using a muslin cloth, producing filtered *L. cretica* leaf extract.

Example 2

Biomimetic Synthesis of AgNPs

About 10 mL of filtered *L. cretica* leaf extract was mixed with about 250 mL of 1 mM $AgNO_3$ and kept at room temperature in a dark place. Color of the reaction mixture changed from colorless to brown, indicating the formation of AgNPs. The mixture containing AgNPs was centrifuged at 15,000 rpm for 20 mM and the supernatant was discarded and the pellet was dispersed in distilled water. This process was repeated three times for removal of impurities and the pellet was dried in an oven at 40° C. The resulting dried *L. cretica* AgNPs were used for further studies.

Example 3

Characterization of AgNPs

Bio-reduction of $Ag^+$ ions to colloidal nanoparticles was visually observed by a color change from colorless ($AgNO_3$ solution) to brown (AgNPs).

UV-Vis spectra were used for further confirmation of the AgNPs synthesis reaction. The absorption of light by the nanoparticles at different wavelengths provides an indication of particle size, while the breadth of the peaks signifies the particle size distribution. FIGS. 1(A) and 1(B) represent the UV spectra recorded at 24 and 48 hours, respectively. The maximum absorbance appears at 440 nm, confirming nanoparticles formation (AgNPs).

Figure 2:
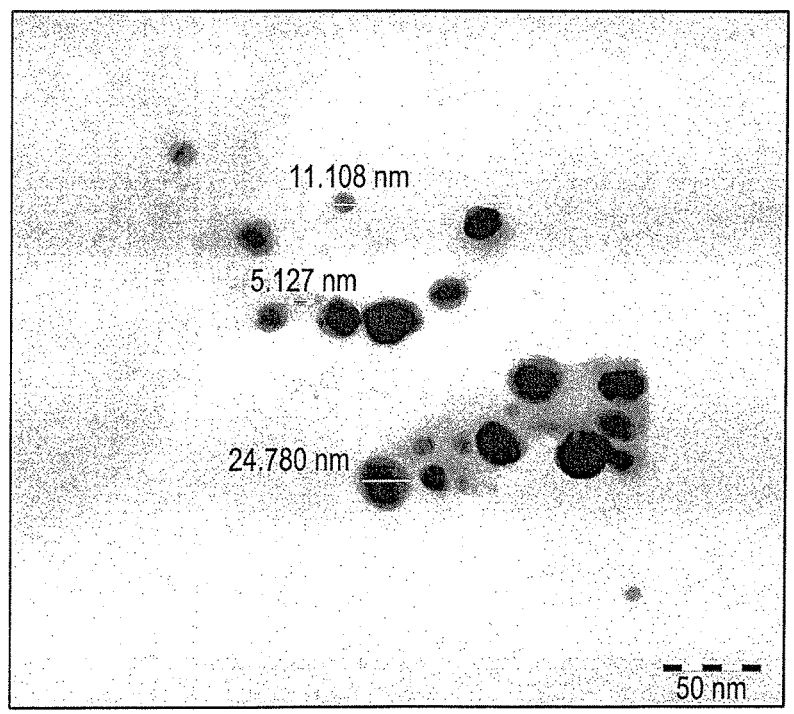
FIG. 2 is a Transmission Electron Microscopy scan of the surface morphology of the *L. cretica* AgNPs.

Formation of nanoparticles was further confirmed by Transmission Electron Microscopy (TEM). FIG. 2 shows that the nanoparticles are spherical in shape with size ranging from 5 nm to 24 nm (average size 11 nm).

Figure 3:
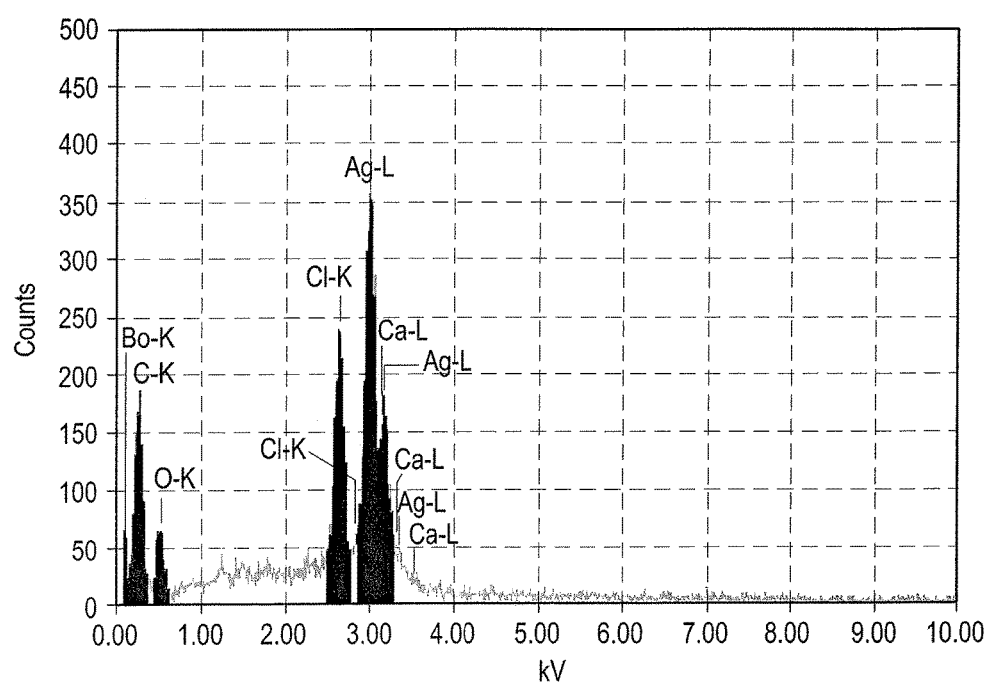
FIG. 3 is an Energy Dispersive X-Ray Diffraction spectrum of *L. cretica* AgNPs, illustrating the additional organic components present.

The presence of additional organic components (*L. cretica* extract components) in the synthesized AgNPs is demonstrated by FIG. 3. The Energy Dispersive X-Ray Diffraction spectra demonstrates intense signal at about 3 keV, confirming the presence of Ag as the major element; however, the spectra also indicates the presence of other elements, including C, O, and Cl. This indicated biomolecules overlapping the silver nanoparticles.

Figure 4:
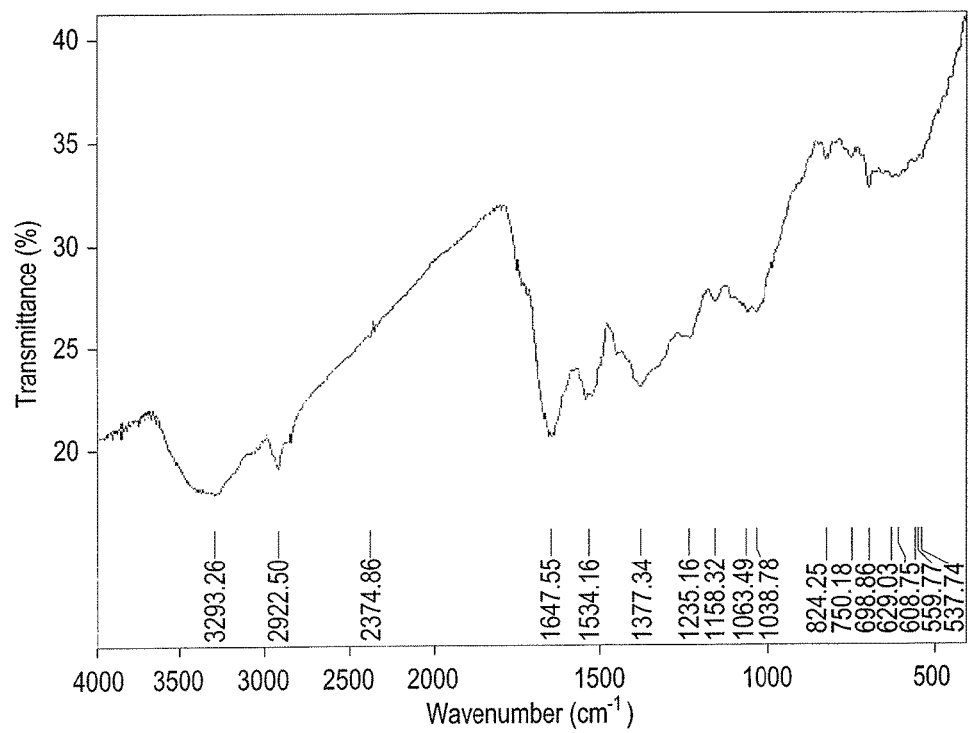
FIG. 4 is a Fourier Transform Infrared Spectroscopy spectrum of the surface functional groups of the *L. cretica* AgNPs.

Fourier Transform Infrared Spectroscopy (FTIR) measurements were performed to identify the biomolecules that bound specifically on the AgNP's surface and the local molecular environment of the capping agent. FIG. 4 presents the FTIR spectra of synthesized AgNPs.

The band at about 3293 $cm^{-1}$ is assigned to the N—H stretch. The band at about 2922 $cm^{-1}$ is assigned to the C—H stretch. The absorption bands observed at about 1647 $cm^1$ are assigned to the amide groups of proteins or to the C═O stretching vibration group. The band at about 1377 $cm^{-1}$ is assigned to the O—H stretch. The bands appearing at about 1038, 1063, 1158 and 1235 $cm^{-1}$ are assigned to the C—O group. The prominent bands at about 750, 698 and 629 $cm^{+1}$ are assigned to the aromatic class. This observed spectrum demonstrates the presence of active biomolecules in the *L. cretica* AgNps.

Figure 5:
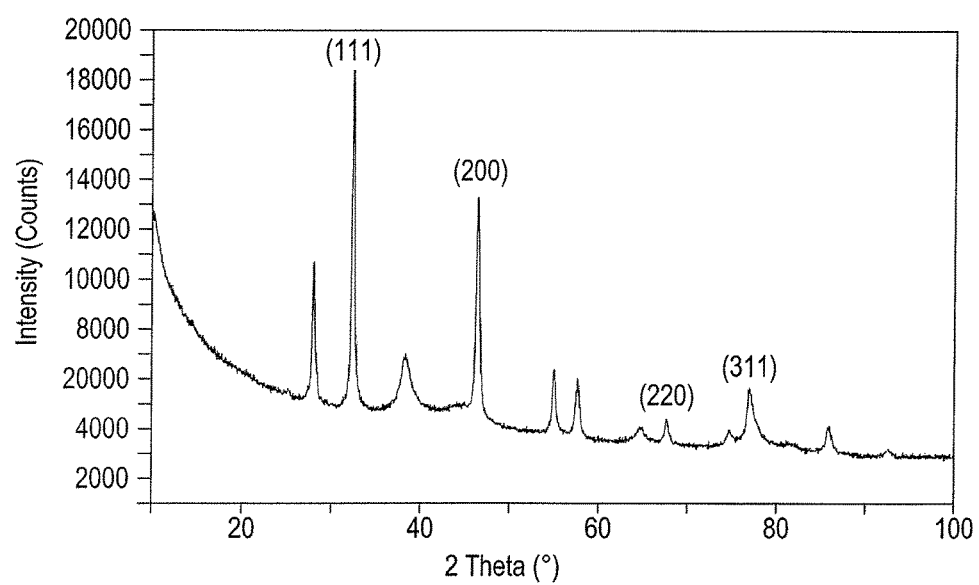
FIG. 5 is an X-Ray Diffraction pattern of the *L. cretica* AgNPs.

The X-Ray Diffraction (XRD) pattern of the *L. cretica* AgNPs is shown in FIG. 5. The crystalline nature of the synthesized AgNPs was confirmed by the XRD analysis. The lattice planes (111), (200), (220) and (311) were indexed for face-centered cubic (fcc) silver.

Example 4

*L. cretica* Leaf AgNPs Antihyperglycemic Effect

Male C57BL/6J mice of 3 weeks of age were maintained under standard conditions with a 12 hour light/dark cycle. The animals received a standard pellet diet and water ad libitum. After an acclimatization period of 1 week, mice were used for experiments. The normal group was provided with a standard pellet diet, which had a fat composition of 4.2%. The high fat diet (HFD) experimental group was provided with beef tallow-based HFD containing 17.7 g protein, 35.8 g fat, 34.5 g carbohydrate, 3.4 g fiber, 6.8 g minerals and 1.8 g vitamins. On the $8^{th}$ week, animals with blood glucose more than 180 mg/dL were considered to be diabetic and were used for the experiment.

The mice were divided into 5 groups, containing 5 mice per group. Group 1 included control mice, and Groups 2, 3, 4, and 5 included diabetic mice. After 6 hours of fasting, 2 g/kg body weight of glucose was loaded orally to all groups. Three doses of *L. cretica* AgNPs (about 500 µg/kg, about 1 mg/kg, and about 2 mg/kg body weight) were given to diabetic mice orally. The OGTT were recorded at 0 mins, 30 mins, 1 hr and 2 hr. Only the active dose of *L. cretica* AgNPs was continued for 15 days' evaluation study.

Figure 6:
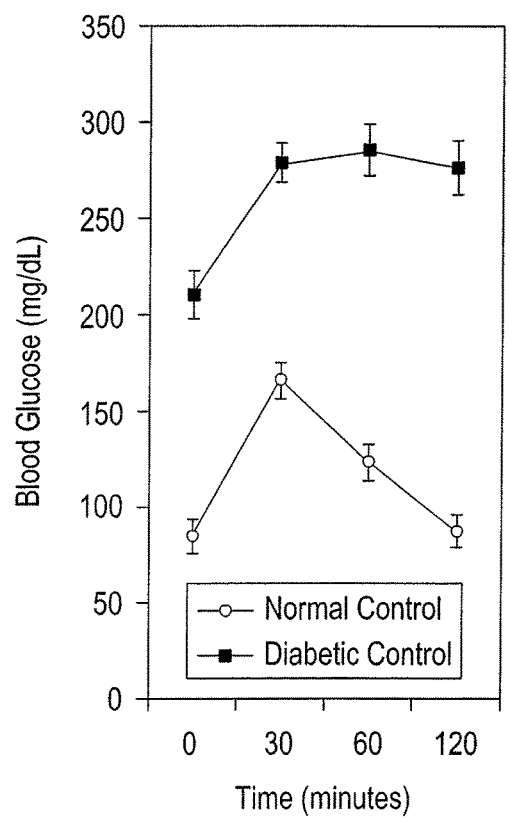
FIG. 6 is a graph of glucose tolerance testing in normal and diabetic control mice.
Figure 7:
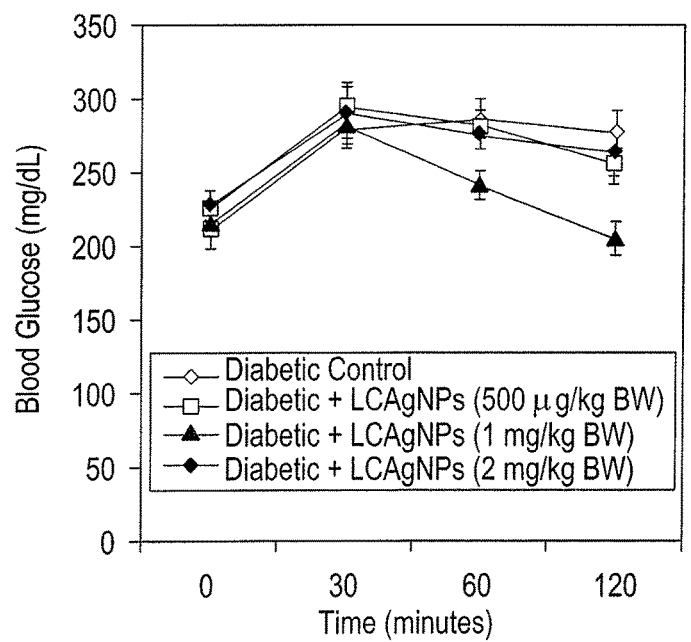
FIG. 7 is a graph of blood glucose over time in diabetic control and diabetic mice treated with different concentrations of *L. cretica* AgNPs.

Analysis of glucose tolerance tests of the different experimental groups is shown in FIG. 6. The results show that in the healthy control or normal control mice there is an increase in blood glucose after the glucose load at the first minute, which then decreases to the baseline level (FIG. 6). In contrast, in diabetic rats with the glucose load, blood glucose levels increased significantly at the first minute and did not return to the baseline level. In diabetic mice treated with *L. cretica* AgNPs, there was no increase in blood glucose levels after the glucose load (FIG. 7). Among the three different doses, the 1 mg/kg dose of *L. cretica* AgNPs showed the maximum prevention of increase in blood glucose levels (FIG. 7). Diabetic rats that were treated with *L. crectica* AgNPs attenuated their increase in blood glucose level in the glucose tolerance test, suggesting that the *L. crectica* AgNPs exert a protective effect (FIG. 7).

Figure 8:
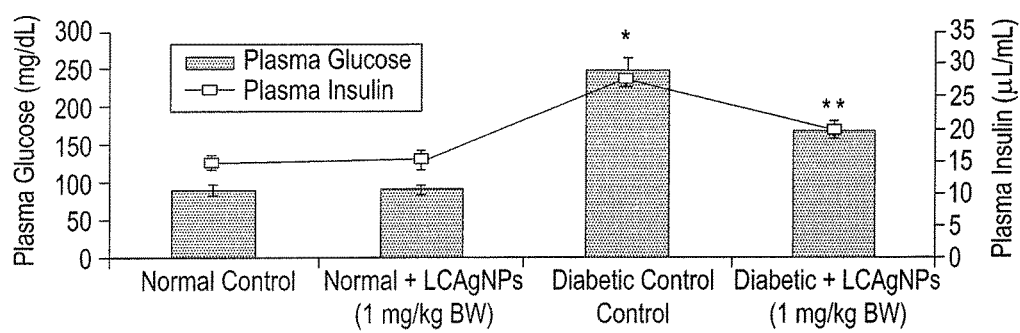
FIG. 8 is a graph of plasma glucose and plasma insulin in control and diabetic mice either treated or untreated with *L. cretica* AgNPs over a period of fifteen days.

Of the three different doses, 1 mg/kg was observed to provide maximum prevention of increase in blood glucose levels. Hence, the 1 mg/kg dose was used for a further 15 days' study. FIG. 8 represents the result of 15 days' treatment of *L. cretica* AgNPs on plasma glucose and insulin in high fat diet (HFD) induced C57BL/6J diabetic mice. As demonstrated in FIG. 8, *L. cretica* AgNP treated HFD-fed diabetic mice demonstrated reduced levels of plasma glucose and insulin when compared to the diabetic controls.

It is to be understood that the biomimetic synthesis of nanoparticles using silver nitrate and *Lavatera cretica* is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of biomimetic synthesis of silver nanoparticles, comprising:
   providing an aqueous extract of *Lavatera cretica* prepared by suspending about 5 g of powdered *Lavatera cretica* in about 500 ml of water for about 24 hours, and
   mixing about 10 ml of the aqueous extract of *Lavatera cretica* with about 250 ml of 1 mM silver nitrate at room temperature to provide silver nanoparticles.

2. The method of biomimetic synthesis of silver nanoparticles of claim 1, wherein the powdered *Lavatera cretica* comprises one or more plant parts of the *Lavatera cretica*.

3. The method of biomimetic synthesis of silver nanoparticles of claim 2, wherein the *Lavatera cretica* plant parts include *Lavatera cretica* leaves.

4. The method of biomimetic synthesis of silver nanoparticles of claim 1, further comprising purifying the silver nanoparticles.

5. The method of biomimetic synthesis of silver nanoparticles of claim 1, wherein the silver nanoparticles have a size ranging from about 5 nm to about 24 nm.

6. The method of biomimetic synthesis of silver nanoparticles of claim 1, wherein the silver nanoparticles have an average size of about 11 nm.

7. The method of biomimetic synthesis of silver nanoparticles of claim 1, further comprising the step of purifying the silver nanoparticles by centrifugation at about 15,000 rpm for about 20 minutes.

8. The method of biomimetic synthesis of silver nanoparticles of claim 7, further comprising the steps of repeating the purifying step at least three times and drying the purified silver nanoparticles in an oven at about 40 degrees Celsius.

9. A nanoparticle composition, comprising:
   silver nanoparticles prepared according to the method of claim 1 and having an average size ranging from about 5 nm to about 24 nm,
   wherein the composition includes silver nanoparticles and *Lavatera cretica* extract components.

10. A method of treating hyperglycemia, comprising administering to a patient in need thereof a therapeutically effective amount of the nanoparticle composition of claim 9.

11. The method of treating hyperglycemia of claim 10, wherein the nanoparticle composition is orally administered to the patient.

12. The method of treating hyperglycemia of claim 10, wherein the therapeutically effective amount of the nanoparticle composition comprises about 1 mg/kg.

* * * * *